United States Patent [19]

Yamada et al.

[11] Patent Number: 5,103,835
[45] Date of Patent: Apr. 14, 1992

[54] IMPEDANCE MONITORING DEVICE FOR PREVENTING URINARY INCONTINENCE

[75] Inventors: Akio Yamada, Higashikurume; Masayoshi Fuse, Machida, both of Japan

[73] Assignee: Nihon Kohden Corporation, Tokyo, Japan

[21] Appl. No.: 691,474

[22] Filed: Apr. 25, 1991

[30] Foreign Application Priority Data

May 2, 1990 [JP] Japan ................................. 2-116294

[51] Int. Cl.$^5$ ............................................. A61B 5/05
[52] U.S. Cl. ................................... 128/734; 128/748; 128/774
[58] Field of Search ............... 128/637, 734, 748, 898, 128/885, 886, 774, DIG. 25, 723, 693; 600/29, 30, 31

[56] References Cited

U.S. PATENT DOCUMENTS

| | | | |
|---|---|---|---|
| 4,852,578 | 8/1989 | Companion et al. | 128/661.03 |
| 4,917,099 | 4/1990 | Stice | 128/696 |
| 4,926,871 | 5/1990 | Ganguly et al. | 128/660.07 |
| 4,969,474 | 12/1990 | Schwarz | 128/885 |
| 4,994,019 | 2/1991 | Fernandez et al. | 600/30 |

Primary Examiner—Max Hindenburg
Assistant Examiner—Guy V. Tucker
Attorney, Agent, or Firm—Hoffmann & Baron

[57] ABSTRACT

A monitoring device for preventing urinary incontinence has the following components: a high-frequency constant-current power supply adapted to supply a pair of terminals which are set on the surface of a human body across the urinary bladder; a high-frequency voltage signal detecting means which conducts wave detection from a high-frequency voltage signal sensed by a pair of sensing electrodes which are set on the human body surface at positions on the path of the high-frequency electrical current flowing between the pair of terminals; a DC component detecting means 13 which detects the DC component of the signal detected by the high-frequency voltage signal detecting means; a variance component detecting means for detecting variance component of the signal detected by the high-frequency voltage signal detecting means; a variance-to-DC ratio computing means for computing the ratio between the DC component and the variance component; and a variance-to-DC ratio evaluating means for activating an informing means when the computed value of the variance-to-DC ratio has reached a predetermined threshold level.

2 Claims, 4 Drawing Sheets

IMPEDANCE MONITORING DEVICE FOR PREVENTING URINARY INCONTINENCE

BACKGROUND OF THE INVENTION

1. Field of the Invention

The present invention relates to a monitoring device which measures the urinary volume in urinary bladder to inform beforehand any possibility of urinary incontinence.

2. Description of the Related Arts

A monitoring device of the kind stated above is known from Japanese Patent Laid-Open No. 63-311952. This known device has a function to measure the positions of the walls of the urinary bladder from the time difference between transmitted and received supersonic waves. When the urinary volume increases in the urinary bladder, the diameter of the bladder increases. It is therefore possible to detect the timing desired to urinate by sensing increase in the above-mentioned time difference.

In another known device, a high-frequency electric current is supplied to flow between a pair of terminals set on the surface of a human body. Another pair of sensor electrodes are disposed in the path of the electrical current. High-frequency voltage signal is picked up by the sensor electrodes. The level of the high-frequency signal is lowered when electrical impedance is decreased due to an increase in the urinary volume in the body. It is thus possible to detect the urinary volume.

The first-mentioned method relies upon detection of displacement of the urinary bladder wall. The displacement of the urinary bladder wall, however, does not properly indicate the urinary volume because the urinary bladder muscle exhibits a complicated behavior in accordance with the increase in the urinary volume. This method, therefore, does not provide high accuracy of detection when displacement of a specific portion of the bladder wall alone is detected. Referring to the second-mentioned method relying upon change in electrical impedance, it is true that the impedance changes in close correlation to the change in the urinary volume. Actually, however, the electrical impedance varies also depending on other factors of the human body. This method, therefore, cannot provide a satisfactorily high accuracy of detection if the detection is conducted by employing specific impedance value as the threshold.

SUMMARY OF THE INVENTION

Accordingly, an object of the present invention is to provide a monitoring device for preventing urinary incontinence which is based upon detection of electrical impedance but is improved to provide a higher accuracy of detection than the known device.

According to the present invention, there is provided a monitoring device for preventing urinary incontinence which not only monitors the change in electrical impedance having correlation to urinary volume but also takes into consideration any change in the electrical impedance caused by expansion and contraction of the urinary bladder attributable to breathing.

The monitoring device of the present invention, therefore, exhibits a higher accuracy of monitoring so as to effectively prevent urinary incontinence. More specifically, the monitoring device of the present invention evaluates the variance-to-DC ratio, i.e., the ratio between the variance component and DC component, of the impedance signal, so that any offset of the base impedance from a standard level, attributable to blooding, edema or the like, can be compensated for because such an offset is canceled in the measured varying impedance. Influence of change in impedance attributable to variation in the state of attaching of the electrodes to the human body is also canceled for the same reason.

It is possible to evaluate also the variations of the base impedance and varying impedance so as to compensate for change in the measuring conditions caused by movement of the human body, thereby contributing to a further improvement in the reliability.

DESCRIPTION OF THE PREFERRED EMBODIMENTS

Figure 1:
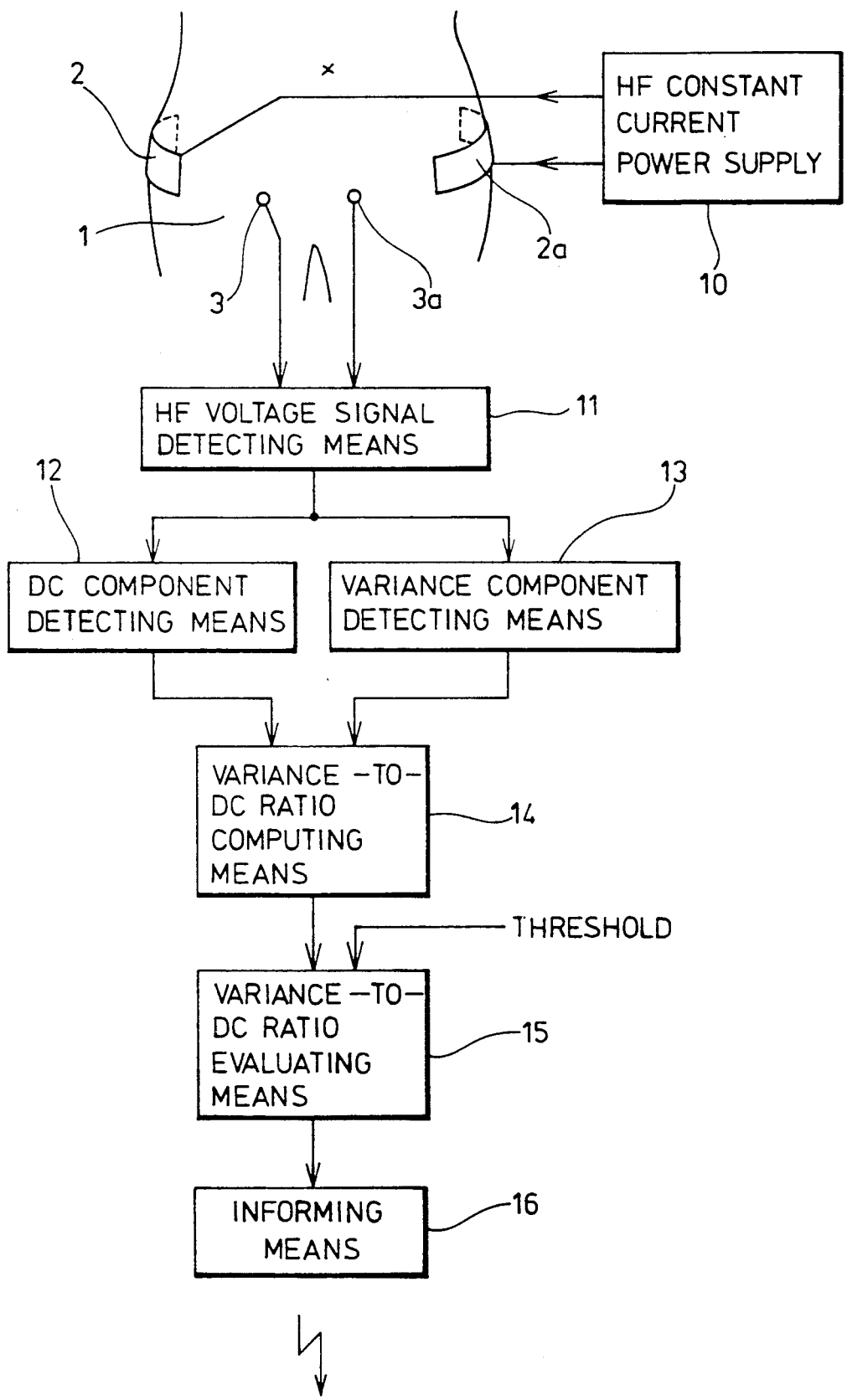
FIG. 1 is a, block diagram showing the circuit arrangement of an embodiment of the monitoring device of the invention for preventing urinary incontinence.

FIG. 1 shows the construction of an embodiment of the monitoring device of the present invention for preventing urinary incontinence.

The device has a high-frequency constant-current power supply 10 adapted to supply a pair of terminals 2, 2a which are set on the surface 1 of a human body across the urinary bladder. The device also has a high-frequency voltage signal detecting means 11 which conducts wave detection from a high-frequency voltage signal sensed by a pair of sensing electrodes 3, 3a which are set on the human body surface 1 at positions on the path of the high-frequency electrical current flowing between the pair of terminals 2, 2a. The device further has a DC component detecting means 12 which detects the DC component $Z_0$ of the detected signal as a base impedance component which corresponds to the bottom envelope of the impedance variation, and a variance component detecting means 13 for detecting variance component $\Delta Z$ as the variance impedance component. The device further has a variance-to-DC ratio computing means 14 for computing the ratio of the variance component $\Delta Z$ to the DC component $Z_0$. The device further has a variance-to-DC component evaluating means 15. The value of the variance-to-DC ratio $\Delta Z/Z_0$ corresponding to a desire to urinate, e.g., an urinary volume of 300 ml or a value at which a specific person feels desire to urinate, is measured beforehand and a threshold value of the ratio is determined beforehand by adding a suitable margin to the measured value. When this threshold value is exceeded by the value calculated by the variance-to-DC component computing means 14, the variance-to-DC component computing means 15 activates an informing means 16 such as a buzzer.

The variance-to-DC ratio computing means 14 and the variance-to-DC evaluating means 15 may be composed of independent circuits which process analog level signals or may be constituted by a CPU which processes digitized $Z_0$ and $\Delta Z$ signals.

Figure 2:
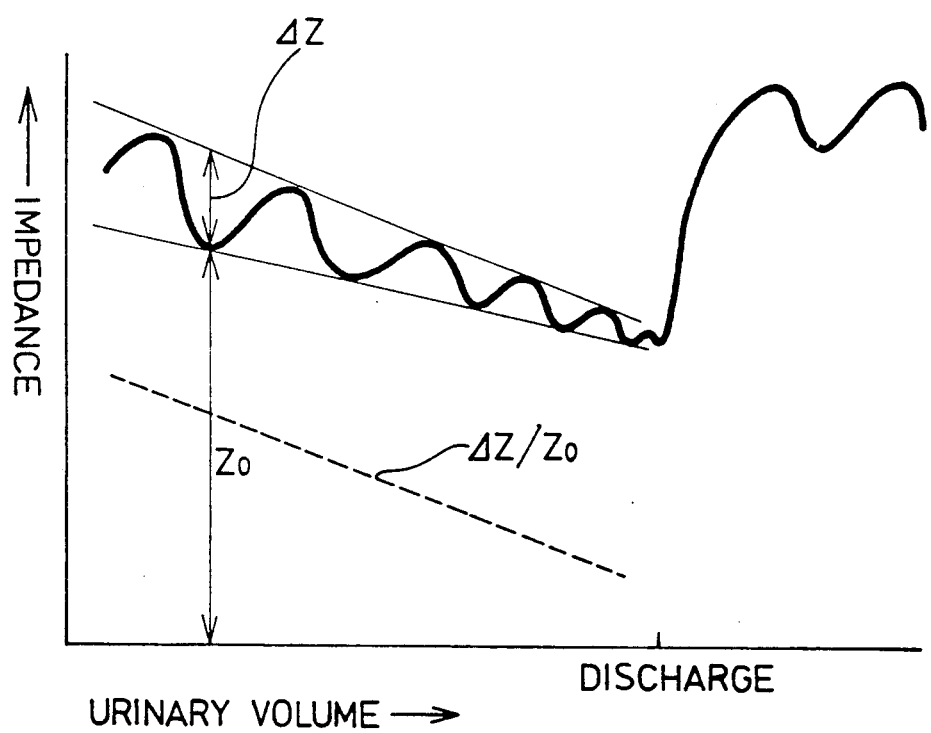
FIG. 2 is a diagram illustrative of operation of the embodiment shown in FIG. 1.

The operation of the monitoring device for preventing urinary incontinence having the described construction will be explained in connection with FIG. 2.

The level of the DC component $Z_0$ reduces as the urinary volume in the urinary bladder increases. In addition, the wall of the urinary bladder is caused to move in accordance with the vertical displacement of the diaphragm as a result of the breathing. The variance $\Delta Z$ of the impedance in the direction of array of electrodes as shown in FIG. 1 is reduced in accordance with the reduction of displacement of the urinary bladder wall corresponding to the increase in the urinary volume. It is to be understood that the period of wave due to breathing is enlarged in FIG. 2. As a consequence, the level of the signal component including the pulsation detected by the high-frequency voltage signal detecting means is lowered in accordance with the increase in the urinary volume. In addition, the variance-to-DC ratio $\Delta Z/Z_0$ becomes to have a greater correlation to the urinary volume because of the drastic reduction in the variance $\Delta Z$, as will be seen from a broken-line curve in FIG. 2. The base impedance $Z_0$ may be reduced due to blooding or presence of an edema, or may be deviated from a standard level corresponding to a certain urinary volume due to variation in the states of fixing of electrodes or due to difference in factors of individual bodies. In such a case, the variance component $\Delta Z$ also varies in accordance with the reduction or deviation of the base impedance, so that any influence of such reduction or deviation is canceled.

The variance-to-DC ratio evaluation means 15, upon detection of the ratio $\Delta Z/Z_0$ having exceeded the threshold level due to increase in the urinary volume, activates the informing means 16 so as to inform the user of the device or an attendant, thereby preventing urinary incontinence.

Figure 3:
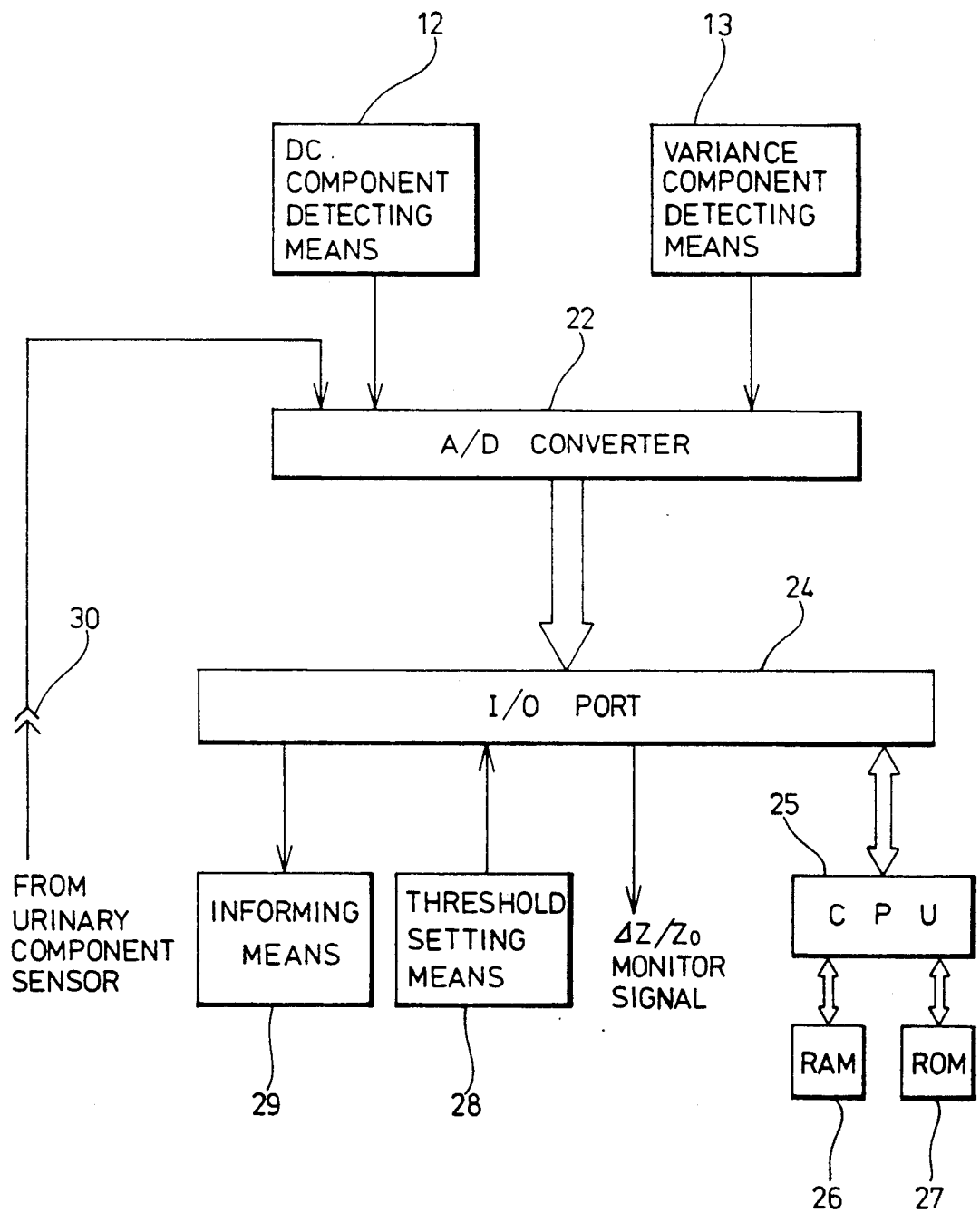
FIG. 3 is a block diagram showing the construction of another embodiment.

FIG. 3 shows another embodiment in which an additional function is provided for determining whether the levels of the DC component and the variance component fall within ordinary ranges corresponding to increase in the urinary volume. More specifically, in this embodiment, the DC component detecting means and the variance component detecting means 12 and 13, which may be the same as those shown in FIG. 1, are connected to a CPU 25 through A/D converters 22 which digitize the signals from the respective detectors 12 and 13. The CPU 25 is provided with an I/O port 24, a ROM 27, a RAM 26 and so forth. The CPU 25 is adapted for delivering an activating signal to informing means 29 through the I/O port 24. A threshold setting means 28 enables an external setting of a threshold value of the ratio $\Delta Z/Z_0$ determined in accordance with the characteristics of the body of the wearer. In addition, a sensing signal derived from an urinary component sensor in the event of urinary discharge is supplied to the CPU from a plug 30 through an A/D converter 22. For instance, the device is set to enable monitoring of the ratio $\Delta Z/Z_0$ with respect to the urinary volume and the volume of urea discharged when a desire to urinate is felt is measured. Then, the value of the ratio $\Delta Z/Z_0$, corresponding to a predetermined proportion, e.g., 80%, of the discharged urinary volume is determined as the threshold value. This threshold value is stored in a battery-backup area of the RAM 26 together with urinary component data as necessitated.

Figure 4:
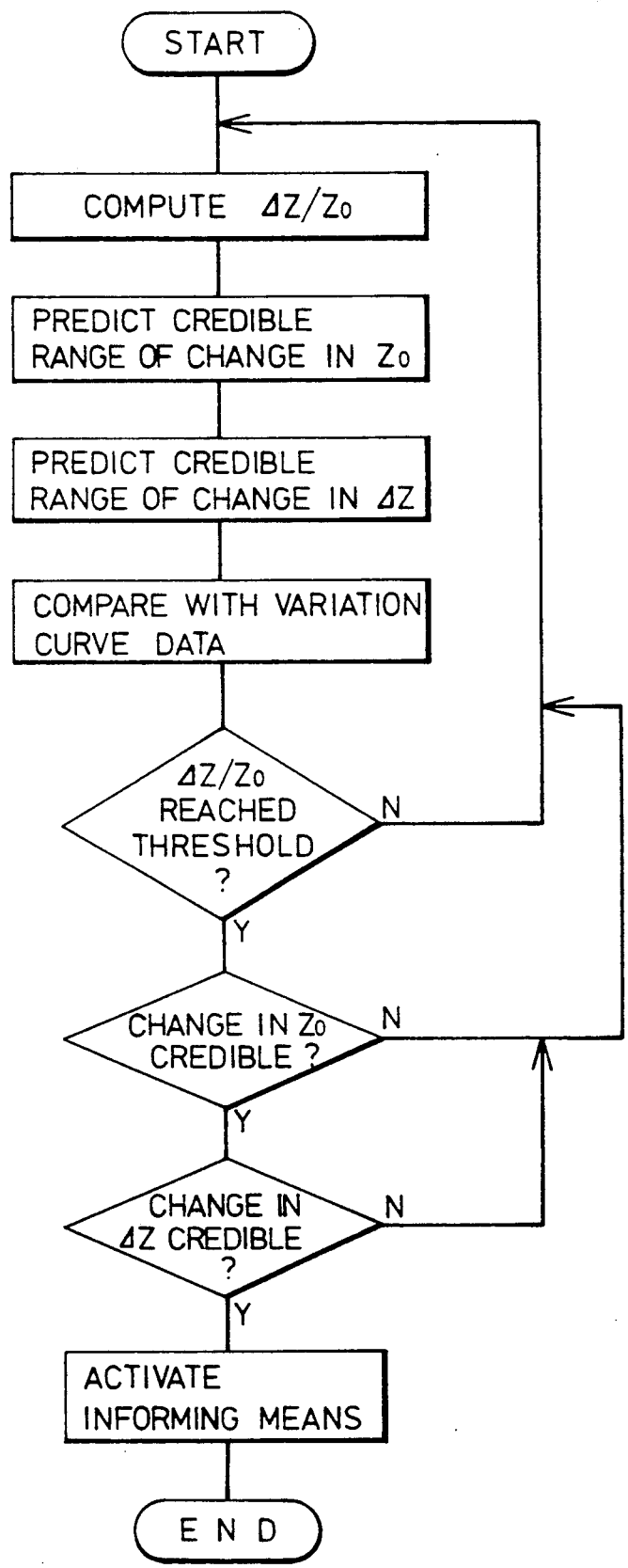
FIG. 4 is a flow chart illustrative of operation of the embodiment shown in FIG. 3.

The CPU 25 operates in cooperation with the RAM 26 and other devices in accordance with a program stored in the ROM 27, following the steps shown in the flowchart of FIG. 4. Namely, the ratio $\Delta Z/Z_0$ is computed in the first step, and variation curve data are formed on the basis of the changes of the $Z_0$ data and $\Delta Z$ data which have been picked up for a predetermined time and determined as being valid. Data values which are successively computed are compared with the above-mentioned variation curve data and future credible ranges of variation of the respective components are predicted for a predetermined time unit, e.g., several minutes. Then, values of $Z_0$ and $Z\Delta$ within the future credible ranges are picked up to enable formation of predict data for further future credible ranges of variation. If urinary component data for dosage of a drug has been taken up, the above-mentioned prediction data should be corrected in accordance with such urinary component data.

According to this arrangement, the activation signal is delivered to the informing means 29 when the continuously monitored value of the ratio $\Delta Z/Z_0$ has reached the threshold, on condition that both the values of the components $Z_0$ and $\Delta Z$ fall within the respective credible ranges. It is therefore possible to eliminate any error in the informing operation attributable to occasional changes in the components $Z_0$ and $\Delta Z$ caused by, for example, movement of the body of the wearer.

In the embodiments described hereinbefore, the electrodes are arrayed laterally of the wearer's body. This, however, is only illustrative and the electrodes may be arrayed in vertical direction or at an inclination with respect to the wearer's body. It has been confirmed that, when the electrodes are arrayed in vertical direction, the variance component $\Delta Z$ of impedance increases in accordance with increase in the urinary volume, unlike the case where the electrodes are arrayed in lateral direction. It is therefore necessary to determine threshold values on the basis of $\Delta Z/Z_0$ curves assumed on various manners of use of the device, so as to further enhance the reliability of operation of the device. To this end, it is advisable to measure the amounts of changes in the $Z_0$ and $\Delta Z$ components in accordance with change in the manner of use of the device.

What is claimed is:

1. A monitoring device for preventing urinary incontinence, comprising:
   a high-frequency constant-current power supply adapted to supply a pair of terminals, which are adopted to be positioned on the surface of a human body so that the current travels across the urinary bladder;
   a pair of sensing electrodes which are adapted to be positioned on the human body surface at positions on the path of the high-frequency electrical current flowing between the said pair of terminals;
   a high-frequency voltage signal detecting means which detects waves from a high-frequency voltage signal sensed by said pair of sensing electrodes;
   a DC component detecting means which detects the DC component of the signal detected by the high-frequency voltage signal detecting means;
   a variance component detecting means which detects the variance component of the signal detected by the high-frequency voltage signal detecting means;
   a variance-to-DC ratio computing means for computing the ratio between the DC component and the variance component; and
   a variance-to-DC ratio evaluating means for activating an informing means when the computed value of the variance-to-DC ratio has reached a predetermined threshold level indicative of a urinary volume at which a specific person feels desire to urinate.

2. A monitoring device according to claim 1, further comprising a DC component variation judging means for judging whether the change in the DC component detected by said DC component detecting means falls within a credible range of change corresponding to increase in urinary volume; and a variance component variation judging means for judging whether the change in the variance component detected by said variance component detecting means falls within a credible range of change corresponding to increase in urinary volume.

* * * * *